US010294272B2

(12) United States Patent
Forssmann et al.

(10) Patent No.: US 10,294,272 B2
(45) Date of Patent: May 21, 2019

(54) PEPTIDES WITH ANTAGONISTIC ACTIVITIES AGAINST NATURAL CXCR4

(71) Applicant: Pharis Biotec GmbH, Hannover (DE)

(72) Inventors: Wolf-Georg Forssmann, Hannover (DE); Frank Kirchhoff, Hannover (DE); Jan Münch, Hannover (DE); Ludger Ständker, Hannover (DE)

(73) Assignee: Pharis Biotec GmbH, Hannover (DE)

( * ) Notice: Subject to any disclaimer, the term of this patent is extended or adjusted under 35 U.S.C. 154(b) by 222 days.

(21) Appl. No.: 14/896,249

(22) PCT Filed: Jun. 12, 2014

(86) PCT No.: PCT/EP2014/062252
§ 371 (c)(1),
(2) Date: Dec. 4, 2015

(87) PCT Pub. No.: WO2014/198834
PCT Pub. Date: Dec. 18, 2014

(65) Prior Publication Data
US 2016/0122389 A1 May 5, 2016

(30) Foreign Application Priority Data

Jun. 12, 2013 (EP) ..................................... 13171718

(51) Int. Cl.
| *A01N 37/18* | (2006.01) |
| *A61K 38/04* | (2006.01) |
| *A61K 38/00* | (2006.01) |
| *A61P 31/12* | (2006.01) |
| *A61P 3/04* | (2006.01) |
| *A61P 25/00* | (2006.01) |
| *A61P 35/00* | (2006.01) |
| *A61K 38/10* | (2006.01) |
| *A61K 38/08* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 7/08* | (2006.01) |
| *C07K 7/06* | (2006.01) |
| *C07K 14/00* | (2006.01) |

(52) U.S. Cl.
CPC .................. *C07K 7/08* (2013.01); *C07K 7/06* (2013.01); *C07K 14/00* (2013.01); *A61K 38/00* (2013.01); *Y02A 50/463* (2018.01); *Y02A 50/465* (2018.01)

(58) Field of Classification Search
None
See application file for complete search history.

(56) References Cited

U.S. PATENT DOCUMENTS

| 8,207,293 | B2 | 6/2012 | Ronjat et al. |
| 9,045,563 | B2 * | 6/2015 | Forssmann .......... C07K 14/765 |
| 2004/0018542 | A1 | 1/2004 | Lanfear et al. |
| 2008/0166364 | A1 | 7/2008 | Bradshaw et al. |

FOREIGN PATENT DOCUMENTS

| JP | 2010531655 A | 9/2010 | |
| JP | 2013519392 A | 5/2013 | |
| RU | 2201421 C2 | 6/2013 | |
| WO | 199429339 A1 | 12/1994 | |
| WO | 2004004054 A2 | 1/2009 | |
| WO | 2009004054 A2 | 1/2009 | |
| WO | WO-2009004054 A2 * | 1/2009 | .......... C07K 14/765 |
| WO | 2011103076 A1 | 8/2011 | |
| WO | 2012112188 A1 | 8/2012 | |
| WO | 2013030320 A1 | 3/2013 | |

OTHER PUBLICATIONS

Alkhatib et al., "CC CKR5: A Rantes, MIP-1α, MIP-1β Receptor as a Fusion Cofactor for Macrophage-Tropic HIV-1", Science, 272:1955-1958 (Jun. 28, 1996).
Bleul et al., "The Lymphocyte Chemoattractant SDF-1 Is a Ligand for LESTR/fusin and Blocks HIV-1 Entry", Nature, 382:829-833 (Aug. 29, 1996).
Brelot et al., "Identification of Residues of CXCR4 Critical for Human Immunodeficiency Virus Coreceptor and Chemokine Receptor Activities", The Journal of Biological Chemistry, 275(31):23736-23744 (Aug. 4, 2000).
Campbell et al., "Chemokines in the Systemic Organization of Immunity", Immunological Review, 195:58-71 (2003).
Deng et al., "Identification of a Major Co-Receptor for Primary Isolates of HIV-1", Nature, 381:661-666 (Jun. 20, 1996).
Dragic et al., "HIV-1 Entry Into CD4+ Cells Is Mediated by the Chemokine Receptor CC-CKR-5", Nature, 381: 667-673 (Jun. 20, 1996).
Engh et al., "Accurate Bond and Angle Parameters for X-Ray Protein Structure Refinement", Acta Cryst., A47: 392-400 (1991).
Feng et al., "HIV-1 Entry Cofactor: Functional cDNA Cloning of a Seven-Transmembrane, G Protein-Coupled Receptor", Science, 272:872-877(May 10, 1996).
Furze et al., "Neutrophil Mobilization and Clearance in the Bone Marrow", Blackwell Publishing Ltd., Immunology, 125:281-288 (2008).
Güntert, "Automated NMR Protein Structure Calculation", Progress in Nuclear Magnetic Resonance Spectroscopy, 43:105-125 (Jun. 23, 2003).
Güntert, "Automated NMR Structure Calculation With CYANA", Methods in Molecular Biology, Protein NMR Techniques, 278:353-378 (2004).

(Continued)

Primary Examiner — Zachary J Miknis
(74) Attorney, Agent, or Firm — Christensen, Fonder, Dardi & Herbert PLLC; Curtis Herbert

(57) ABSTRACT

A peptide effective in blocking the CXC-chemokine receptor 4 (CXCR4) mediated HIV-1 NL4-3 (X4-tropic) infection with an $IC_{50}$ value of less than 50 μM.

11 Claims, No Drawings

Specification includes a Sequence Listing.

(56) References Cited

OTHER PUBLICATIONS

Hachet-Haas et al., "Small Neutralizing Molecules to Inhibit Actions of the Chemokine CXCL12*", The Journal of Biological Chemistry, 283(34):23189-23199 (Aug. 22, 2008).

Herrmann et al., "Protein NMR Structure Determination With Automated NOE Assignment Using the New Software CANDID and the Torsion Angle Dynamics Algorithm DYANA", Journal Molecular Biology, 319:209-227 (2002).

Huang et al., "Molecular Dynamics Simulations on SDF-1α: Binding With CXCR4 Receptor", Biophysical Journal, 84:171-184 (Jan. 2003).

Kuil et al., "Hybrid Peptide Dendrimers for Imaging of CXCR4 Expression", Molecular Pharmaceutics, 8(6):2444-2453 (Dec. 5, 2011).

MacDonald et al., "Solid-Phase Synthesis of Phosphonylated Peptides", Synlett, 13:1951-1954 (2010).

Margolis et al., "Selective Transmission of CCR5-Utilizing HIV-1: 'TheGatekeeper' Problem Resolved?", Nature, 4:312-317 (Apr. 2006).

Moepps et al., "Two Murine Homologues of the Human Chemokine Receptor CXCR4 Mediating Stromal Cell-Derived Factor 1α Activation of Gi2 Are Differentially Expressed In Vivo", European Journal Immunology, 27: 2102-2112 (1997).

Möhle et al., "G Protein-Coupled Receptor Crosstalk and Signaling in Hematopoietic Stem and Progenitor Cells", Annals of the New York Academy of Sciences, 1266:63-67 (2012).

Mohty et al., "In and Out of the Niche, Perspectives in Mobilization of Hematopoietic Stem Cells", Experimental Hermatology, 39:723-729 (2011).

Moon et al., "Allergen-Induced CD11b+ CD11cint CCR3+ Macrophages in the Lung Promote Eosinophilic Airway Inflammation in a Mouse Asthma Model", International Immunology, 19(12):1371-1381 (Apr. 11, 2007).

Nagasawa et al., "Defects of B-Cell Lymphopoiesis and Bone-Marrow Myelopoiesis in Mice Lacking the CXC Chemokine PBSF/SDF-1", Nature, 382:635-638 (Aug. 15, 1996).

Ratajczak et al., "The Use of Chemokine Receptor Agonists in Stem Cell Mobilization", Expert Opinion, Biology Thesis, 12(3):287-297 (2012).

Schroeder et al., "Mobilization of Hematopoietic Stem and Leukemia Cells", Journal of Leukocyte Biology, 91:47-57 (Jan. 2012).

Tachibana et al., "The Chemokine Receptor CXCR4 Is Essential for Vascularization of the Gastrointestinal Tract", Nature, 393:591-594 (Jun. 11, 1998).

Valenzuela-Fernandez et al., "Optimal Inhibition of X4 HIV Isolates by the CXC Chemokine Stromal Cell-Derived Factor 1α Requires Interaction With Cell Surface Heparan Sulfate Proteoglycans*", The Journal of Biology Chemistry, 276(28):26550-26558 (May 4, 2001).

Zhou et al., "Structural and Functional Characterization of Human CXCR4 as a Chemokine Receptor and HIV-1 Co-Receptor by Mutagenesis and Molecular Modeling Studies", The Journal of Biology Chemistry, 276(46): 42826-42833 (Nov. 16, 2001).

Zou et al., "Function of the Chemokine Receptor CXCR4 in Haematopoiesis and in Cerebellar Development", Nature, 393:595-599 (Jun. 11, 1998).

Japanese Application No. 2016-518492 Office Action, dated Jan. 23, 2018, Mailing No. 022494. 4 pages.

* cited by examiner

SEQUENCE LISTING

```
<160> NUMBER OF SEQ ID NOS: 28

<210> SEQ ID NO 1
<211> LENGTH: 11
<212> TYPE: PRT
<213> ORGANISM: artificial
<220> FEATURE:
<223> OTHER INFORMATION: peptide derived from the human albumin sequence

<400> SEQUENCE: 1

Ile Val Arg Tyr Ser Lys Lys Val Pro Gln Cys
1               5                   10

<210> SEQ ID NO 2
<211> LENGTH: 12
<212> TYPE: PRT
<213> ORGANISM: artificial
<220> FEATURE:
<223> OTHER INFORMATION: peptide derived from human albumin sequence

<400> SEQUENCE: 2

Ile Val Arg Tyr Thr Lys Cys Val Pro Gln Val Ser
1               5                   10
```

<210> SEQ ID NO 3
<211> LENGTH: 12
<212> TYPE: PRT
<213> ORGANISM: artificial
<220> FEATURE:
<223> OTHER INFORMATION: peptide derived from human albumin sequence

<400> SEQUENCE: 3

Ile Val His Tyr Thr Lys Lys Val Pro Gln Val Ser
1               5                   10

<210> SEQ ID NO 4
<211> LENGTH: 12
<212> TYPE: PRT
<213> ORGANISM: artificial
<220> FEATURE:
<223> OTHER INFORMATION: peptide derived from human albumin sequence

<400> SEQUENCE: 4

Ile Val Lys Tyr Thr Lys Lys Val Pro Gln Val Ser
1               5                   10

<210> SEQ ID NO 5
<211> LENGTH: 12
<212> TYPE: PRT
<213> ORGANISM: artificial
<220> FEATURE:
<223> OTHER INFORMATION: peptide derived from human albumin sequence

<400> SEQUENCE: 5

Ile Val Arg Tyr Ser Lys Lys Val Pro Gln Val Ser
1               5                   10

<210> SEQ ID NO 6
<211> LENGTH: 12
<212> TYPE: PRT
<213> ORGANISM: artificial
<220> FEATURE:
<223> OTHER INFORMATION: peptide derived from human albumin sequence

<400> SEQUENCE: 6

Ile Val Arg Tyr Thr Lys Lys Val Pro Gln Cys Ser
1               5                   10

<210> SEQ ID NO 7
<211> LENGTH: 12
<212> TYPE: PRT
<213> ORGANISM: artificial
<220> FEATURE:
<223> OTHER INFORMATION: peptide derived from human albumin sequence

<400> SEQUENCE: 7

Ile Val Arg Trp Thr Lys Lys Val Pro Gln Val Cys
1               5                   10

<210> SEQ ID NO 8
<211> LENGTH: 12
<212> TYPE: PRT
<213> ORGANISM: artificial
<220> FEATURE:
<223> OTHER INFORMATION: peptide derived from human albumin sequence

<400> SEQUENCE: 8

Ile Val Arg Trp Thr Cys Lys Val Pro Gln Val Ser
1               5                   10

```
<210> SEQ ID NO 9
<211> LENGTH: 12
<212> TYPE: PRT
<213> ORGANISM: artificial
<220> FEATURE:
<223> OTHER INFORMATION: peptide derived from human albumin sequence

<400> SEQUENCE: 9

Ile Val Arg Trp Cys Lys Lys Val Pro Gln Val Ser
1               5                   10

<210> SEQ ID NO 10
<211> LENGTH: 12
<212> TYPE: PRT
<213> ORGANISM: artificial
<220> FEATURE:
<223> OTHER INFORMATION: peptide derived from human albumin sequence

<400> SEQUENCE: 10

Ile Val Arg Trp Ser Lys Lys Val Pro Gln Cys Ser
1               5                   10

<210> SEQ ID NO 11
<211> LENGTH: 12
<212> TYPE: PRT
<213> ORGANISM: artificial
<220> FEATURE:
<223> OTHER INFORMATION: peptide derived from human albumin sequence

<400> SEQUENCE: 11

Ile Val Arg Trp Ser Lys Lys Val Pro Cys Val Ser
1               5                   10

<210> SEQ ID NO 12
<211> LENGTH: 12
<212> TYPE: PRT
<213> ORGANISM: artificial
<220> FEATURE:
<223> OTHER INFORMATION: peptide derived from human albumin sequence

<400> SEQUENCE: 12

Ile Val Arg Trp Ser Lys Lys Val Cys Gln Val Ser
1               5                   10

<210> SEQ ID NO 13
<211> LENGTH: 12
<212> TYPE: PRT
<213> ORGANISM: artificial
<220> FEATURE:
<223> OTHER INFORMATION: peptides derived from human albumin sequence

<400> SEQUENCE: 13

Ile Val Arg Phe Thr Lys Lys Val Pro Gln Val Ser
1               5                   10

<210> SEQ ID NO 14
<211> LENGTH: 12
<212> TYPE: PRT
<213> ORGANISM: artificial
<220> FEATURE:
<223> OTHER INFORMATION: peptides derived from human albumin sequence

<400> SEQUENCE: 14

Ile Val Arg Ser Thr Lys Lys Val Pro Gln Val Ser
1               5                   10

<210> SEQ ID NO 15
```

```
<211> LENGTH: 12
<212> TYPE: PRT
<213> ORGANISM: artificial
<220> FEATURE:
<223> OTHER INFORMATION: peptides derived from human albumin sequence

<400> SEQUENCE: 15

Ile Val Arg Trp Thr Lys Lys Val Pro Gln Val Ser
1               5                   10

<210> SEQ ID NO 16
<211> LENGTH: 16
<212> TYPE: PRT
<213> ORGANISM: artificial
<220> FEATURE:
<223> OTHER INFORMATION: peptides derived from human albumin sequence

<400> SEQUENCE: 16

Leu Val Arg Tyr Thr Lys Lys Val Pro Gln Val Ser Thr Pro Thr Leu
1               5                   10                  15

<210> SEQ ID NO 17
<211> LENGTH: 15
<212> TYPE: PRT
<213> ORGANISM: artificial
<220> FEATURE:
<223> OTHER INFORMATION: peptides derived from human albumin sequence

<400> SEQUENCE: 17

Leu Val Arg Tyr Thr Lys Lys Val Pro Gln Val Ser Thr Pro Thr
1               5                   10                  15

<210> SEQ ID NO 18
<211> LENGTH: 14
<212> TYPE: PRT
<213> ORGANISM: artificial
<220> FEATURE:
<223> OTHER INFORMATION: peptides derived from human albumin sequence

<400> SEQUENCE: 18

Leu Val Arg Tyr Thr Lys Lys Val Pro Gln Val Ser Thr Pro
1               5                   10

<210> SEQ ID NO 19
<211> LENGTH: 13
<212> TYPE: PRT
<213> ORGANISM: artificial
<220> FEATURE:
<223> OTHER INFORMATION: peptides derived from human albumin sequence

<400> SEQUENCE: 19

Leu Val Arg Tyr Thr Lys Lys Val Pro Gln Val Ser Thr
1               5                   10

<210> SEQ ID NO 20
<211> LENGTH: 12
<212> TYPE: PRT
<213> ORGANISM: artificial
<220> FEATURE:
<223> OTHER INFORMATION: peptides derived from human albumin sequence

<400> SEQUENCE: 20

Leu Val Arg Tyr Thr Lys Lys Val Pro Gln Val Ser
1               5                   10

<210> SEQ ID NO 21
<211> LENGTH: 11
```

```
<212> TYPE: PRT
<213> ORGANISM: artificial
<220> FEATURE:
<223> OTHER INFORMATION: peptides derived from human albumin sequence

<400> SEQUENCE: 21

Leu Val Arg Tyr Thr Lys Lys Val Pro Gln Val
1               5                   10

<210> SEQ ID NO 22
<211> LENGTH: 10
<212> TYPE: PRT
<213> ORGANISM: artificial
<220> FEATURE:
<223> OTHER INFORMATION: peptides derived from human albumin sequence

<400> SEQUENCE: 22

Leu Val Arg Tyr Thr Lys Lys Val Pro Gln
1               5                   10

<210> SEQ ID NO 23
<211> LENGTH: 8
<212> TYPE: PRT
<213> ORGANISM: artificial
<220> FEATURE:
<223> OTHER INFORMATION: peptides derived from human albumin sequence

<400> SEQUENCE: 23

Leu Val Arg Tyr Thr Lys Lys Val
1               5

<210> SEQ ID NO 24
<211> LENGTH: 13
<212> TYPE: PRT
<213> ORGANISM: artificial
<220> FEATURE:
<223> OTHER INFORMATION: peptides derived from human albumin sequence

<400> SEQUENCE: 24

Leu Leu Val Arg Tyr Thr Lys Lys Val Pro Gln Val Ser
1               5                   10

<210> SEQ ID NO 25
<211> LENGTH: 12
<212> TYPE: PRT
<213> ORGANISM: artificial
<220> FEATURE:
<223> OTHER INFORMATION: peptides derived from human albumin sequence

<400> SEQUENCE: 25

Ile Val Arg Tyr Thr Lys Lys Val Pro Gln Val Ser
1               5                   10

<210> SEQ ID NO 26
<211> LENGTH: 8
<212> TYPE: PRT
<213> ORGANISM: artificial
<220> FEATURE:
<223> OTHER INFORMATION: peptides derived from human albumin sequence

<400> SEQUENCE: 26

Leu Val Arg Tyr Ala Lys Lys Val
1               5

<210> SEQ ID NO 27
<211> LENGTH: 8
<212> TYPE: PRT
```

```
<213> ORGANISM: artificial
<220> FEATURE:
<223> OTHER INFORMATION: peptides derived from human albumin sequence

<400> SEQUENCE: 27

Leu Ala Arg Tyr Thr Lys Lys Val
1               5

<210> SEQ ID NO 28
<211> LENGTH: 9
<212> TYPE: PRT
<213> ORGANISM: artificial
<220> FEATURE:
<223> OTHER INFORMATION: peptides derived from human albumin sequence

<400> SEQUENCE: 28

Leu Val Arg Tyr Thr Lys Lys Val Pro
1               5
```

PEPTIDES WITH ANTAGONISTIC ACTIVITIES AGAINST NATURAL CXCR4

CROSS REFERENCE TO RELATED APPLICATIONS

This application is a national stage filing of PCT Application No. PCT/EP2014/062252, filed June 12, 2014, which claims priority to European Application No.: 13171718.3, June 12, 2013, all of which are incorporated herein by reference.

TECHNICAL FIELD

The present invention concerns peptides with antagonistic activities against natural CXCR4, therapeutic uses of the peptides of the invention as well as a method for manufacturing the peptides of the invention.

BACKGROUND OF THE INVENTION

The CXC chemokine receptor 4 (CXCR4) is a G protein-coupled receptor (GPCR) with stromal cell-derived factor-1 (SDF-1 or CXCL12) as sole published ligand. CXCR4 is involved in multiple developmental and physiological processes including stem cell homing (Möhle and Drost, 2012) and migration of immune cells (Campbell et al., 2003). The CXCR4-CXCL12 axis also plays a role in innate and adaptive immunity, as well as in various disease processes, such as cancer cell metastasis, leukemia cell migration, rheumatoid arthritis and pulmonary fibrosis (Nagasawa et al., 1996; Zou et al., 1998; Tachibana et al. 1998; Furze et al., 2008). Man-made CXCR4 antagonists are capable of mobilizing hematopoietic stems cells (HSCs), which are utilized for immune reconstitution after organ transplantation or chemotherapy (Ratajczak and Kim, 2012; Schroeder and DiPersio, 2012). In addition, CXCR4 is also a major co-receptor for HIV-1 entry into target cells (Feng et al., 1996; Bleul et al., 1996). Co-receptor utilization of CXCR4 is highly effective and a high proportion of CD4+ T cells express this GPCR in lymphatic tissues in vivo. Nonetheless, almost exclusively HIV-1 variants utilizing the C—C chemokine receptor type 5 (CCR5) are transmitted and found during chronic HIV-1 infection (Alkhatib et al., 1996; Deng et al., 1996; Dragic et al., 1996). It has been proposed that multiple factors contribute to the inefficient transmission of CXCR4-tropic (X4) HIV-1 strains (Margolis and Shattock, 2006). However, the mechanism(s) underlying the effective control of X4 HIV-1 in immunocompetent individuals remain poorly understood.

Research on CXCR4-antagonists has recently become an immense field of projects due to the manifold indications In particular the efforts to find a strategy to intervene with cancer cell proliferation, differentiation, and metastasis was not so successful in clinical studies yet as expected. The development of one of the compound groups, namely AMD3100 a CXCR4-antagonists

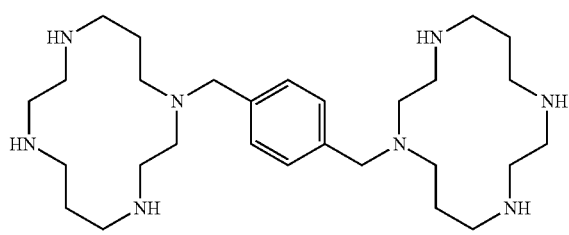 [SMILES: c1cc(CN2CCCNCCNCCCNCC2)ccc1CN1CCCNCCNCCCNCC1]

(a bicyclame compound: Hendrix and Flexner 2000), had to be stopped for long term treatments due to toxic side effects. Although AMD is registered for single short applications in stem cell mobilisation, it is nevertheless a challenge to find adequate antagonists to the target CXCR4.

SUMMARY OF THE INVENTION

The aim of the present invention is accomplished by a peptide effective in blocking X4 tropic HIV-1 NL4-3 infection with an $IC_{50}$ value of less than 50 µM having the general amino acid sequence $$Z^1\ X\ X^0\ X^1\ X^2\ X^3\ X^4\ X^5\ V\ X^6\ X^7\ X^8\ X^9\ Z^2$$

except the peptides consisting of the amino acid sequences of SEQ ID NOs 16-28, wherein X=I, P or L, <E, if $Z^1$=0 then X=I, dL, dI, V, W, S, T, Val, Cap, β-L, β-I, Sul-L, Sul-I, Sul-V, $X^0$=V or, if X=I then $X^0$ is either V or d-V, d-L, d-I, d-M, d-P, β-V, β-L, β-I, β-M, β-P, or Sul-V $X^1$=R, H or K;

$X^2$=Y, F, S or W;

$X^3$=A, T, C or S;

$X^4$ and $X^5$=K or C with the proviso that $X^4$=C then $X^5 \neq$C is and if $X^5$=C then $X^4 \neq$C;

$X^6$=P, C or a deletion, and both $X^4$ and $X^5$=K;

$X^7$=Q, C or a deletion;

$X^8$=C, V or a deletion;

$X^9$=S, C or is a deletion, $Z^1$=0, L, $Z^2$, or <E, wherein $Z^2$=0 or a modification of the N-terminal nitrogen atom of the peptide chain which modification forms together with the amino group of the N-terminal amino acid of the peptide a moiety having the structure —$NR^2R^3$ wherein $R^2$ and/or $R^3$ are independently from each other H or a substituted or unsubstitued acyl alkyl, aryl, aralkyl, cyclo alkyl and heterocyclo alkyl group;

$Z^3$=0, TPTE-$Z^4$, TPT-$Z^4$, TP-$Z^4$, T-$Z^4$, or $Z^4$, wherein $Z^4$=0 or is a modification of the C-terminal carboxyl group of the peptide chain which modification forms together with the carboxyl group of the C-terminal amino acid of the peptide a moiety having the structure —C(O)—O—$R^1$ or —C(O)—$NR^2R^3$ wherein $R^1$ is a substituted or unsubstitued alkyl, aryl, aralkyl, cyclo alkyl and heterocyclo alkyl group; and wherein further abbreviations have the following meaning: Cap=caproic acid (C6 carboxylic acid), <E=pyro gutamate, Val=valeric acid (C5 carboxylic acid), and Sul=sulfon amino acids.

The skilled person understands that the term "comprising" or "having" can be replaced by "consisting of" without adding new matter.

The present invention demonstrates that the peptide of the invention affects T cell migration and stem cell mobilization as well as inhibits bacterial pathogens. Thus, the peptide of the invention is a natural CXCR4 antagonist that may prevent the transmission of X4 HIV-1 strains and plays a role in regulating CXCR4 activity and anti-microbial immunity in vivo.

In a preferred embodiment of the invention the peptide of the invention comprises the general amino acid sequence $$Z^1\ X\ X^0\ R\ X^2\ X^3\ X^4\ X^5\ V\ X^6\ X^7\ X^8\ X^9\ Z^3$$

except the peptides consisting of the amino acid sequences of SEQ ID NOs 16-28,
wherein
X=I, or if $Z^1$=0 then X=I, dL, dI, V, W, S, T, Val, Cap, β-L, β-I, Sul-L, Sul-I, Sul-V,
$X^0$=V or d-V, d-L, d-I, d-M, d-P, β-V, β-L, β-I, β-M, β-P, or Sul-V
$X^2$=Y, or W;
$X^3$=T, C or S;
$X^4$ and $X^5$=K or C with the proviso that $X^4$=C then $X^5 \neq$C is and if $X^5$=C then $X^4 \neq$C;
$X^6$=P, C or a deletion, and both $X^4$ and $X^5$=K;
$X^7$=Q, C or a deletion;
$X^8$=C, V or a deletion;
$X^9$=S, C or is a deletion,
$Z^1$=0, L, $Z^2$, or <E, wherein $Z^2$=0 or a modification of the N-terminal nitrogen atom of the peptide chain which modification forms together with the amino group of the N-terminal amino acid of the peptide a moiety having the structure —$NR^2R^3$ wherein $R^2$ and/or $R^3$ are independently from each other H or a substituted or unsubstitued acyl alkyl, aryl, aralkyl, cyclo alkyl and heterocyclo alkyl group;
$Z^3$=0, or $Z^4$, wherein
$Z^4$=0 or is a modification of the C-terminal carboxyl group of the peptide chain, except Aca which modification forms together with the carboxyl group of the C-terminal amino acid of the peptide a moiety having the structure —C(O)—O—$R^1$ or —C(O)—$NR^2R^3$ wherein $R^1$ is a substituted or unsubstitued alkyl, aryl, aralkyl, cyclo alkyl and heterocyclo alkyl group; and
wherein further abbreviations have the following meaning:
Cap=caproic acid (C6 carboxylic acid), Aca=amino caproic acid, <E=pyro gutamate, Val=valeric acid (C5 carboxylic acid), and Sul=sulfon amino acids.

In another preferred embodiment of the invention the peptide of the invention comprises the following sequence of amino acids:

I V $X^1$ $X^2X^3$ $X^4$ $X^5$ V $X^6$ $X^7$ $X^8$ $X^9$ wherein
$X^1$=R, H or K;
$X^2$=Y, F, S or W;
$X^3$=T, C or S;
$X^4$=K or C;
$X^5$=K or C;
$X^6$=P or if $X^1$=R and $X^2$=W and $X^3$=S and $X^4$=K and $X^5$=K, then $X^6$=C;
$X^7$=Q or C;
$X^8$=V or C;
$X^9$=S, C or if $X^1$=R and $X^2$=Y and $X^3$=S and $X^4$=K and $X^5$=K, then
$X^9$ is a Deletion.

In yet another embodiment the peptide of the invention comprises the following sequence of amino acids

I V R $X^2X^3$ $X^4$ $X^5$ V $X^6$ $X^7$ $X^8$ $X^9$ wherein
$X^2$=Y, or W;
$X^3$=T, C or S;
$X^4$=K or C;
$X^5$=K or C;
$X^6$=P or if $X^1$=R and $X^2$=W and $X^3$=S and $X^4$=K and $X^5$=K, then $X^6$=C;
$X^7$=Q or C;
$X^8$=V or C;
$X^9$=S, C or if $X^1$=R and $X^2$=Y and $X^3$=S and $X^4$=K and $X^5$=K, then
$X^9$ is a deletion.

In a still further embodiment of the present invention the peptide of the invention is selected from the group consisting of peptide having at least one of the following amino acid sequence:

```
                                        (SEQ ID NO: 13)
IVRFTKKVPQVS,   408I-419  Y411F (SEQ ID NO: 14)
IVRWTKKVPQVS,   408I-419  Y411W (SEQ ID NO: 15)
IVRYSKKVPQVS,   408I-419  T412S.
```

It can be stated that the substitution of $X^2$=Tyr by Trp or dimerisation of these peptides have a lower $IC_{50}$ which could not be expected by the skilled person.

Yet another embodiment of the invention comprises the peptide of the invention having at least one of the following amino acid sequence:

```
                                        (SEQ ID NO: 2)
IVRYTKCVPQVS,   408I-419  K414C (SEQ ID NO: 1)
IVRYSKKVPQC,    408I-418  SC (SEQ ID NO: 7)
IVRWTKKVPQVC,   408I-419  WC01

(SEQ ID NO: 8)
IVRWTCKVPQVS,   408I-419  WC02

(SEQ ID NO: 9)
IVRWCKKVPQVS,   408I-419  WC03

(SEQ ID NO: 10)
IVRWSKKVPQCS,   408I-419  WSC01

(SEQ ID NO: 11)
IVRWSKKVPCVS,   408I-419  WSC02

(SEQ ID NO: 12)
IVRWSKKVCQVS,   408I-419  WSC03

(SEQ ID NO: 6)
IVRYTKKVPQCS,   408I-419  V418C.
```

Particularly useful peptides of the present invention are dimeric peptides consisting of two identical monomeric peptides according to the invention which peptides comprise the amino acid cysteine, wherein the dimeric peptides are linked to each other via a cysteine bridge which is formed between the monomeric peptides. In particular the dimeric peptide of the invention the monomeric peptides comprising the amino acid Cystein are selected from the group of peptides having the following amino acid sequence:

```
                                        (SEQ ID NO: 2)
IVRYTKCVPQVS,   408I-419  K414C (SEQ ID NO: 1)
IVRYSKKVPQC,    408I-418  SC (SEQ ID NO: 7)
IVRWTKKVPQVC,   408I-419  WC01
```

-continued

```
                                          (SEQ ID NO: 8)
IVRWTCKVPQVS, 408I-419 WC02

(SEQ ID NO: 9)
IVRWCKKVPQVS, 408I-419 WC03

(SEQ ID NO: 10)
IVRWSKKVPQCS, 408I-419 WSC01

(SEQ ID NO: 11)
IVRWSKKVPCVS, 408I-419 WSC02

(SEQ ID NO: 12)
IVRWSKKVCQVS, 408I-419 WSC03

(SEQ ID NO: 6)
IVRYTKKVPQCS, 408I-419 V418C.
```

Subject matter of the invention are also peptides of the invention for use in the treatment of neurological diseases, in particular stroke, Parkinson's disease, Alzheimer's disease, multiple sklerosis; in the field of immunology in particular for the treatment of the WHIm-syndrom and rheumatoide arthritis; in the field of oncology in particular for the treatment of cancers, in particular cancers showing the CRCX receptor such as cancer of the liver, pancress, prostate, or breast cancer; for the treatment of lack of mobilization, proliferation and migration of stem cells, T-cell activation as well as support of immunoblasts such as CTL/PD-1; in the treatment of wounds caused by burning; for the treatment of antifibrosis; treatment or prevention of scars; for treatment of cardiologic disorders, in particular heart insufficiency; for the treatment of metabolic disorders, in particular diabetes;

wherein the peptide is effective in blocking X4 tropic HIC-1 NL4-3 infection with an $IC_{50}$ value of less than 50 μM with the formula $$Z^1 \ X \ X^0 \ X^1 \ X^2 \ X^3 \ X^4 \ X^5 \ V \ X^6 \ X^7 \ X^8 \ X^9 \ Z^3$$

and wherein

X=I, P or L, <E, if $Z^1$=0 then X=I, dL, dI, V, W, S, T, Val, Cap, β-L, β-I, Sul-L, Sul-I, Sul-V, $X^0$=V or, if X=I then $X^0$ is either V or d-V, d-L, d-I, d-M, d-P, β-V, β-L, β-I, β-M, β-P, or Sul-V $X^1$=R, H or K, in particular $X^1$=R;

$X^2$=Y, F, S or W;

$X^3$=A, T, C or S;

$X^4$ and $X^5$=K or C with the proviso that $X^4$=C then $X^5 \neq$C is and if $X^5$=C then $X^4 \neq$C;

$X^6$=P, C or a deletion, and both $X^4$ and $X^5$=K;

$X^7$=Q, C or a deletion;

$X^8$=C, V or a deletion;

$X^9$=S, C or is a deletion, $Z^1$=0, L, $Z^2$, or <E, wherein $Z^2$=0 or a modification of the N-terminal nitrogen atom of the peptide chain which modification forms together with the amino group of the N-terminal amino acid of the peptide a moiety having the structure —$NR^2R^3$ wherein $R^2$ and/or $R^3$ are independently from each other H or a substituted or unsubstitued acyl alkyl, aryl, aralkyl, cyclo alkyl and heterocyclo alkyl group;

$Z^3$=0, TPTE-$Z^4$, TPT-$Z^4$, TP-$Z^4$, T-$Z^4$, or $Z^4$, wherein $Z^4$=0 or is a modification of the C-terminal carboxyl group of the peptide chain which modification forms together with the carboxyl group of the C-terminal amino acid of the peptide a moiety having the structure —C(O)—O—$R^1$ or —C(O)—$NR^2R^3$ wherein $R^1$ is a substituted or unsubstitued alkyl, aryl, aralkyl, cyclo alkyl and heterocyclo alkyl group; and wherein further abbreviations have the following meaning: Cap=caproic acid (C6 carboxylic acid), <E=pyro gutamate, Val=valeric acid (C5 carboxylic acid), and Sul=sulfon amino acids.

Subject matter of the present invention are also peptides of the invention for use in the treatment of neurological diseases, in particular stroke, Parkinson's disease, Alzheimer's disease, multiple sklerosis; in the field of immunology in particular for the treatment of the WHIM-syndrom and rheumatoide arthritis; in the field of oncology in particular for the treatment of cancers, in particular cancers showing the CRCX receptor such as cancer of the liver, pancreas, prostate, or breast cancer; for the treatment of disorders of hematopoiesis, in particular for support of the mobilization, proliferation and migration of stem cells, T-cell activation as well as support of immunoblasts such as CTL/PD-1; in the treatment of wounds, in particular wounds caused by burning; for the treatment of antifibrosis; treatment or prevention of scars; for treatment of cardiologic disorders, in particular heart insufficiency; for the treatment of metabolic disorders, in particular diabetes; for the treatment of viral diseases, in particular infections with HIV-I, HIV-2, Cytomegalo virus, Herpes simplex virus (type 1 and 2), Varicella zoster virus, Hepatitis A and Hepatitis B virus, Influenza virus, Polio virus, Rhino virus, Rubella virus, Measles virus, Rabies virus, Rous sarcoma virus, Epstein-Barr Virus; and for the treatment of infections caused by bacteria and fungi, in particular *Pseudomonas, Candida, S. aureus*; for the treatment of infectious processes, abnormal infectious processes; treatment of growth disorders, treatment of neuronal diseases, disorders of the blood clotting cascade and hematopoiesis, vascular diseases, diseases of the immune system, and for improving wound and bone healing.

A further subject matter of the present invention is a method for the manufacturing of at least one of the peptides of the invention by solid phase syntheses.

Furthermore, subject matter of the present invention is also a method for the manufacturing of at least one of the peptides of the invention, wherein monomeric peptides are provided and coupled under oxidative reaction conditions which are capable to oxidize SH bonds to yield —S—S— bonds.

DETAILED DESCRIPTION OF THE INVENTION

The invention is further described in more detail using the peptide of SEQ ID NO 16 as a typical representative of the peptide of the invention. In addition to the disclosure of the present invention it is referred to in WO 2009/004054 A2, incorporated by reference.

The peptide of the invention is effective in blocking X4 tropic HIC-1 NL4-3 infection with an $IC_{50}$ value of less than 50 μM. Those peptides are regarded as having the sufficient inhibitory effect to suppress or inhibit the physiological responses mediated by the active CXCR4. The peptides of the invention comprise the general amino acid sequence $$Z^1 \ X \ X^0 \ X^1 \ X^2 \ X^3 \ X^4 \ X^5 \ V \ X^6 \ X^7 \ X^8 \ X^9 \ Z^2$$

except the peptides consisting of the amino acid sequences of SEQ ID NOs 16-28. The exclusion of the peptides of the sequences of SEQ ID NOs 16-28 is due to the fact that they are disclosed in WO 2009/004054 A2 and overlap with the general amino acid sequence of the peptides of the invention. However, the peptides of the invention as well as those of SEQ ID NOs 16-28 can be used as medicaments for use in the treatment of neurological diseases, in particular stroke, Parkinson's disease, Alzheimer's disease, multiple sklerosis; in the field of immunology in particular for the treatment of the WHIM-syndrom and rheumatoide arthritis; in the field of oncology in particular for the treatment of cancers, in particular cancers showing the CXCR4 receptor such as cancer of the liver, pancreas, prostate, or breast cancer; for the treatment of lack of mobilization, proliferation and migration of stem cells, T-cell activation as well as support of immunoblasts such as CTL/PD-1; in the treatment of wounds caused by burning; for the treatment of antifibrosis; treatment or prevention of scars; for treatment of cardiologic disorders, in particular heart insufficiency; for the treatment of metabolic disorders, in particular diabetes.

In the formula of the peptide of the invention the following definitions are valid:

X=I, P or L. Also <E which represents, pyro gutamate can replace I, P or L in order to protect the N-terminal of the peptide against proteolytic attacks. Alternatively, if $Z^1$ is not present the N-terminal amino acid may be selected from the group consisting of, dL, dI, β-L, β-I, sulfon amino acids (Sul), such as Sul-L, Sul-I, Sul-V, V, W, S, and T; or from caproic acid (C6 carboxylic acid), valeric acid (C5 carboxylic acid).

The other positions of the amino acid sequence are as follows:

$X^0$=V or, if X=I then $X^0$ is either V or d-V, d-L, d-I, d-M, d-P, β-V, β-L, β-I, β-M, β-P, or Sul-V $X^1$=R, H or K, in particular $X^1$=R;

$X^2$=Y, F, S or W;

$X^3$=A, T, C or S;

$X^4$ and $X^5$=K or C with the proviso that $X^4$=C then $X^5 \neq$C is and if $X^5$=C then $X^4 \neq$C;

$X^6$=P, C or a deletion, and both $X^4$ and $X^5$=K;

$X^7$=Q, C or a deletion;

$X^8$=C, V or a deletion;

$X^9$=S, C or is a deletion.

The N-terminal group $Z^1$ is, if present, L, $Z^2$, or <E, wherein $Z^2$=0 or a modification of the N-terminal nitrogen atom of the peptide chain which modification forms together with the amino group of the N-terminal amino acid of the peptide a moiety having the structure —$NR^2R^3$ wherein $R^2$ and/or $R^3$ are independently from each other H or a substituted or unsubstitued acyl alkyl, aryl, aralkyl, cyclo alkyl and heterocyclo alkyl group;

the C terminal group $Z^3$=0, TPTE-$Z^4$, TPT-$Z^4$, TP-$Z^4$, T-$Z^4$, or $Z^4$, wherein $Z^4$=0 or is a modification of the C-terminal carboxyl group of the peptide chain which modification forms together with the carboxyl group of the C-terminal amino acid of the peptide a moiety having the structure —C(O)—O—$R^1$ or —C(O)—$NR^2R^3$ wherein $R^1$ is a substituted or unsubstitued alkyl, aryl, aralkyl, cyclo alkyl and heterocyclo alkyl group. The further abbreviations have the following meaning:

Cap=caproic acid (C6 carboxylic acid), <E=pyro gutamate, Val=valeric acid (C5 carboxylic acid), and Sul=sulfon amino acids.

Also retro-inverso peptides of the peptides of the invention are in the scope of the present invention, as well as other derivatives stabilizing the peptide bond against peptidases.

The term derivative means all length fragments including truncations at the N and C terminus, the peptide of the invention containing amino acid residue substitutions including D-amino acid residues and modified amino acid residues as well as peptides containing disulfide bonds and extension at the N and C terminus.

The present invention demonstrates that the peptide of the invention affects T cell migration and stem cell mobilization as well as inhibits bacterial pathogens. Thus, the peptide of the invention is a natural CXCR4 antagonist that may prevent the transmission of X4 HIV-1 strains and plays a role in regulating CXCR4 activity and anti-microbial immunity in vivo.

In a preferred embodiment of the invention the peptide of the invention comprises the following sequence of amino acids:

$$I \quad V \quad X^1 \quad X^2 X^3 \quad X^4 \quad X^5 \quad V \quad X^6 \quad X^7 \quad X^8 \quad X^9$$

wherein $X^1$=R, H or K, in particular $X^1$=R;

$X^2$=Y, F, S or W;

$X^3$=T, C or S;

$X^4$=K or C;

$X^5$=K or C;

$X^6$=P or if $X^1$=R and $X^2$=W and $X^3$=S and $X^4$=K and $X^5$=K, then $X^6$=C;

$X^7$=Q or C;

$X^8$=V or C;

$X^9$=S, C or if $X^1$=R and $X^2$=Y and $X^3$=S and $X^4$=K and $X^5$=K, then $X^9$ is a deletion.

In a still further embodiment of the present invention the peptide of the invention is selected from the group consisting of peptide having at least one of the following amino acid sequence:

```
                                      (SEQ ID NO: 13)
IVRFTKKVPQVS, 408I-419 Y411F (SEQ ID NO: 15)
IVRWTKKVPQVS, 408I-419 Y411W (SEQ ID NO: 5)
IVRYSKKVPQVS, 408I-419 T412S.
```

Yet another embodiment of the invention comprises the peptide of the invention having at least one of the following amino acid sequence:

```
                                      (SEQ ID NO: 2)
IVRYTKCVPQVS, 408I-419 K414C (SEQ ID NO: 1)
IVRYSKKVPQC,  408I-418  SC (SEQ ID NO: 7)
IVRWTKKVPQVC, 408I-419 WC01

(SEQ ID NO: 8)
IVRWTCKVPQVS, 408I-419 WC02

(SEQ ID NO: 9)
IVRWCKKVPQVS, 408I-419 WC03

(SEQ ID NO: 10)
IVRWSKKVPQCS, 408I-419 WSC01

(SEQ ID NO: 11)
IVRWSKKVPCVS, 408I-419 WSC02
```

```
                                (SEQ ID NO: 12)
    IVRWSKKVCQVS, 408I-419 WSC03

(SEQ ID NO: 6)
    IVRYTKKVPQCS, 408I-419 V418C.
```

Particularly useful peptides of the present invention are dimeric peptides consisting of two identical monomeric peptides according to the invention which peptides comprise the amino acid cysteine, wherein the dimeric peptides are linked to each other via a cysteine bridge which is formed between the monomeric peptides. In particular the dimeric peptide of the invention the monomeric peptides comprising the amino acid Cystein are selected from the group of peptides having the following amino acid sequence:

```
                                 (SEQ ID NO: 2)
    IVRYTKCVPQVS, 408I-419 K414C (SEQ ID NO: 1)
    IVRYSKKVPQC,  408I-418 SC (SEQ ID NO: 7)
    IVRWTKKVPQVC, 408I-419 WC01

(SEQ ID NO: 8)
    IVRWTCKVPQVS, 408I-419 WC02

(SEQ ID NO: 9)
    IVRWCKKVPQVS, 408I-419 WC03

(SEQ ID NO: 10)
    IVRWSKKVPQCS, 408I-419 WSC01

(SEQ ID NO: 11)
    IVRWSKKVPCVS, 408I-419 WSC02

(SEQ ID NO: 12)
    IVRWSKKVCQVS, 408I-419 WSC03

(SEQ ID NO: 6)
    IVRYTKKVPQCS, 408I-419 V418C.
```

Subject matter of the present invention are also peptides of the invention for use in the treatment of neurological diseases, in particular stroke, Parkinson's disease, Alzheimer's disease, multiple sklerosis; in the field of immunology in particular for the treatment of the WHIM-syndrom and rheumatoide arthritis; in the field of oncology in particular for the treatment of cancers, in particular cancers showing the CRCX receptor such as cancer of the liver, pancreas, prostate, or breast cancer; for the treatment of disorders of hematopoiesis, in particular for support of the mobilization, proliferation and migration of stem cells, T-cell activation as well as support of immunoblasts such as CTL/PD-1; in the treatment of wounds, in particular wounds caused by burning; for the treatment of antifibrosis; treatment or prevention of scars; for treatment of cardiologic disorders, in particular heart insufficiency; for the treatment of metabolic disorders, in particular diabetes; for the treatment of viral diseases, in particular infections with HIV-I, HIV-2, Cytomegalo virus, Herpes simplex virus (type 1 and 2), Varicella zoster virus, Hepatitis A and Hepatitis B virus, Influenza virus, Polio virus, Rhino virus, Rubella virus, Measles virus, Rabies virus, Rous sarcoma virus, Epstein-Barr Virus; and for the treatment of infections caused by bacteria and fungi, in particular *Pseudomonas, Candida, S. aureus*; for the treatment of infectious processes, abnormal infectious processes; treatment of growth disorders, treatment of neuronal diseases, disorders of the blood clotting cascade and hematopoiesis, vascular diseases, diseases of the immune system, and for improving wound and bone healing.

The peptide of the invention can be formulated as medicament with suitable pharmaceutically acceptable carriers.

The peptide according to the invention can be administered in a way usual for peptides on a parenteral, intravenous, intramuscular, intranasal, local-topic, subcutaneous or buccal route. The amount of peptide to be administered is from 1 µg to 1 g per unit dose per day.

A further subject matter of the present invention is a method for the manufacturing of at least one of the peptides of the invention by solid phase syntheses. The chemical synthesis of the peptide of the invention can be performed by means of conventional solid-phase synthesis for example on a peptide synthesizer 9050 (Applied Biosystems) using the known Fmoc chemistry.

Furthermore, subject matter of the present invention is also a method for the manufacturing of at least one of the peptides of the invention, wherein monomeric peptides are provided and coupled under oxidative reaction conditions which are capable to oxidize SH bonds to yield —S—S— bonds.

Antiviral screening was performed using the X4 HIV-1 NL4-3 molecular clone. To determine whether the antiviral activity was dependent on the viral coreceptor tropism and to exclude the possibility that a contaminating agent was responsible for the observed effects, we next tested the effect of chemically synthesized the peptide of SEQ ID NO 16 on a variety of HIV-1 strains. The synthetic peptide generally inhibited infection by X4 HIV-1 strains with a mean 50% inhibitory concentration ($IC_{50}$) of 15.8 µg/ml (corresponding to 8.6 µM). Replication of wild-type (wt) HIV-1 NL4-3 in PBMCs was markedly suppressed at concentrations ≥4 µg/ml. Notably, just ~1% of the highly abundant HSA precursor needs to be converted to the peptide of the peptide of SEQ ID NO 16 to achieve ~10 µg/ml. the peptide of the peptide of SEQ ID NO 16 did not display cytotoxic effects even at exceedingly high concentrations. Further experiments confirmed that the peptide also inhibits infection by X4 HIV-2 and SIV strains, although the effects were relatively modest since these viruses utilize multiple coreceptors. We found that pretreatment of viral target cells but not of virions resulted in effective reduction of HIV infection, suggesting that the peptide of SEQ ID NO 16 has a cellular target. Furthermore, the potency of inhibition gradually decreased if the peptide of SEQ ID NO 16 was added after exposure of the cells to the virions, and the HSA precursor had no antiretroviral effect. Thus, the data demonstrate that a fragment of the most abundant protein in human plasma is a naturally occurring and specific inhibitor of X4 HIV-1 strains that targets an early step of the viral life cycle.

It has been found that the peptide of SEQ ID NO 16 competes with CXCL12 binding to CXCR4 in a dose-dependent manner. The dissociation constant ($DC_{50}$) equaled 8±3 µM, corresponding to a $K_I$ value of 3±1 µM. Thus, the $DC_{50}$ value of the peptide of SEQ ID NO 16 is similar to the $IC_{50}$ values obtained in HIV-1 inhibition assays. As noted above, however, these concentrations can easily be achieved by proteolytic cleavage of a small fraction of the abundant HSA precursor.

It was examined whether the peptide of SEQ ID NO 16 affects CXCR4/CXCL12-mediated cellular migration, which plays a key role in homeostasis, immune responses and the metastasis of various cancers. It has been found that the peptide of SEQ ID NO 16 suppressed CXCL12-induced migration of Jurkat T cells as well as of CD34+ human stem cells. Similarly, the peptide of SEQ ID NO 16 prevented tumor cell invasion in vitro. Thus, this peptide may exert anti-inflammatory as well as anti-invasive and anti-metastatic effects.

The CXCL12-CXCR4 axis is involved in bone marrow retention of hematopoietic stem cells (HSCs), which are commonly used for the reconstitution of hematopoiesis in transplant patients (Mohty et al., 2011). Human and mouse CXCR4 are highly conserved and pilot studies in mice revealed that a single i.p. administration of the peptide of SEQ ID NO 16 resulted in a significant mobilization of progenitor cells and neutrophils into the periphery. Transplantation of cells derived from the peptide of SEQ ID NO 16 treated mice resulted in increased engraftment rates, further supporting successful mobilization of stem cells by this naturally occurring peptide.

An i.p. administration of the peptide of SEQ ID NO 16 significantly reduced CXCR4-dependent infiltration of neutrophils, lymphocytes and eosinophils into the airways of mice upon allergen challenge with OVA. This treatment also markedly reduced infiltration of macrophages. In contrast, ALB409-423, which does not interact with CXCR4, had no significant effects. Thus, the peptide of SEQ ID NO 16 is an effective antagonist of CXCR4 in vivo that mobilizes stem cells and exerts anti-inflammatory effects in mouse models.

It has been found that the peptide of SEQ ID NO 16 inhibited *Pseudomonas aeroginosa*, a gram negative opportunistic pathogen, in a dose-dependent manner and was 80% effective at concentrations ≥5 μM. In comparison, only modest effects were observed against *Staphylococus aureus*, a gram-positive bacterial pathogen, or *Candida albicans*, a diploid fungus and causal agent of opportunistic oral and genital infections. Thus, the peptide of SEQ ID NO 16 not only inhibits X4 HIV-1 strains but also exerts specific anti-bacterial effects.

The interaction of the peptide of SEQ ID NO 16 with CXCR4 is highly specific since the activity of a large number of other GPCRs was not affected and that this peptide interacts with the second extracellular loop of CXCR4. The exact process of the peptide of SEQ ID NO 16 binding to CXCR4 remains to be determined. It has been reported that CXCL12 initially interacts with the N-terminus of CXCR4 to induce conformational changes which subsequently allow the interaction of the ligand with the second and third extracellular loops of the GPCR (Brelot et al., 2000; Zhou et al., 2001; Huang et al., 2003).

| SEQ ID NO | Derivative | SEQuence | IC50 (μM) |
|---|---|---|---|
| 16 | 408-423 | LVRYTKKVPQVSTPTL | 8.63 |
| 17 | 408-422 | LVRYTKKVPQVSTPT | 13.4 |
| 18 | 408-421 | LVRYTKKVPQVSTP | 14.0 |
| 19 | 408-420 | LVRYTKKVPQVST | 15.3 |
| 20 | 408-419 | LVRYTKKVPQVS | 5.49 |
| 21 | 408-418 | LVRYTKKVPQV | 26.8 |
| 22 | 408-417 | LVRYTKKVPQ | 19.8 |
| 23 | 408-415 | LVRYTKKV | 25.7 |
| 24 | 407-419 | LLVRYTKKVPQVS | 11.1 |
| 25 | 408I-419 | IVRYTKKVPQVS | 2.48 |
| 26 | 408-415-T412A | LVRYAKKV | 11.2 |
| 27 | 408-415-V409A | LARYTKKV | 32.9 |
| 28 | 408-416 | LVRYTKKVP | n.d. |
| 3 | 408I-419 R410H | IVHYTKKVPQVS | >100* |
| 4 | 408I-419 R410K | IVKYTKKVPQVS | >100* |
| 13 | 408I-419 Y411F | IVRFTKKVPQVS | 3.89 |
| 14 | 408I-419 Y411S | IVRSTKKVPQVS | >100* |
| 15 | 408I-419 Y411W | IVRWTKKVPQVS | 1.54 |
| 5 | 408I-419 T412S | IVRYSKKVPQVS | 2.09 |
| 2 | 408I-419 K414C | IVRYTCVPQVS | 5.87 |
| 6 | 408I-419 V418C | IVRYTKKVPQCS | 3.69 |
| 1 | 408I-418 SC | IVRYSKKVPQC | 2.94 |
| 7 | 408I-419 WC01 | IVRWTKKVPQVC | 1.65 |
| 8 | 408I-419 WC02 | IVRWTCKVPQVS | 2.10 |
| 9 | 408I-419 WC03 | IVRWCKKVPQVS | 1.82 |
| 10 | 408I-419 WSC01 | IVRWSKKVPQCS | 0.87 |
| 11 | 408I-419 WSC02 | IVRWSKKVPCVS | 0.31 |
| 12 | 408I-419 WSC03 | IVRWSKKVCQVS | 1.51 |
| 2 | 408I-419 K414C x2 | (IVRYTCVPQVS)$_2$ | 1.05 |
| 6 | 408I-419 V418C x2 | (IVRYTKKVPQCS)$_2$ | 0.46 |
| 7 | 408I-419 WC01_x2 | (IVRWTKKVPQVC)$_2$ | 0.40 |
| 8 | 408I-419 WC02 x2 | (IVRWTCKVPQVS)$_2$ | 0.32 |
| 9 | 408I-419 WC03 x2 | (IVRWCKKVPQVS)$_2$ | 0.60 |
| 1 | 408I-418 SC x2 | (IVRYSKKVPQC)$_2$ | 0.39 |
| 10 | 408I-419 WSC01 x2 | (IVRWSKKVPQCS)$_2$ | 0.18 |
| 11 | 408I-419 WSC02 x2 | (IVRWSKKVPCVS)$_2$ | 0.12 |
| 12 | 408I-419 WSC03 x2 | (IVRWSKKVCQVS)$_2$ | n.d. |

*due to an I050 of >50 μM not a peptide of the invention

EXAMPLES

Peptides

The peptide of SEQ ID NO 16 and various derivates thereof were synthesized by conventional solid-phase synthesis on a peptide synthesizer 9050 (Applied Biosystems) using Fmoc chemistry. The peptide was purified by RP chromatography, and its identity and purity were established by analytical RP-HPLC and MALDI-MS.

Virus Stocks

HIV-1, HIV-2 and SIV molecular clones differing in coreceptor tropism were generated by transient transfection of 293T cells with proviral DNA by the calcium phosphate method (CalPhos™ Mammalian Transfection Kit, Clontech). After overnight incubation, the transfection mixture was replaced by DMEM medium supplemented with 10% FCS, and virus stocks were harvested 48 hrs post-transfection. Subsequently, the culture supernatant was centrifuged for 5 min at 3000 rpm to remove cell debris. The resulting virus stock was quantified by p24 (HIV) or p27 (SIV) antigen ELISA. Virus stocks were either used immediately or stored in aliquots at −80° C.

TZM-bl Infection Assay

TZM-bl reporter cells containing the LacZ reporter gene under the control of the HIV-1 promoter were seeded in 96-well F-bottom microtiter plates (Greiner Bio-One). On the following day, the cells were preincubated with various dilutions of the peptide of SEQ ID NO 16 or its derivatives for 1 hour and subsequently infected with HIV-1, HIV-2, and SIV. Infection rates were determined after 2 days using the one-step Tropix Gal-Screen Kit, as recommended by the manufacturer.

PBMC Infection Assay

Peripheral blood mononuclear cells were isolated from Buffy coat derived from the DRK-Blutspendedienst Baden-Württemberg-Hessen using Ficoll density centrifugation. $1 \times 10^6$ PBMC per ml were stimulated with 1 µg/ml phytohemagglutinine (PHA, Oxoid, #3085280) and 10 ng/ml Interleukin 2 (IL-2, Strathmann, #9511192) for three days. Thereafter, cells were pelleted and resuspended in IL-2 containing medium. $2 \times 10^5$ PBMC were seeded in 96 well F-bottom microtiter plates, peptides were added and cells were infected with 10-100 µg p24 antigen of X4 or R5 tropic viruses. Supernatants containing progeny virus were taken at every 2-3 days post infection. Virus production was measured by p24 antigen ELISA (NIH AIDS reagent program). The mean p24 antigen values (ng/ml) were derived from triplicate infections±standard deviation.

Cell Viability

To assess cytotoxic effects TZM-bl cells or prestimulated PBMCs were incubated with increasing concentrations of peptides. Cell viability was determined using the CellTiter-Glo Luminescent Cell Viability Assay (PROMEGA, G7571) as recommended by the manufacturer. Values were derived from triplicate measurements. Vitality rates were calculated relative to ATP levels in PBS (no peptide) containing cells (100%). Data were recorded using a luminometer 10 minutes after adding reagent.

The peptide of the peptide of SEQ ID NO 16 blocks an early step in infection

Real-Time Fluorescence Monitoring of Ligand-Receptor Interactions

Anti-human CXCR4 (clone 12G5, IgG2a) or anti-human CXCR7 (clone 9C4) monoclonal antibodies (mAbs) were purchased from R&D Systems (Minneapolis, Minn.). The binding of unconjugated anti-CXCR7 and anti-CXCR4 mAbs was revealed using a PE-conjugated goat anti-mouse F(ab')2 Ab (Dako, Glostrup, Denmark) and analyzed on a FACSCalibur flow cytometer (BD Bio-sciences) with the CellQuest software. The human chemokines CXCL12 and CXCL12-TexasRed were synthesized as described (Valenzuela-Fernandez, et al. 2001). The human chemokine CXCL11 was purchased from Cliniscences SAS (France).

Experiments were performed using cells stably expressing eGFP-CXCR4, suspended in HEPES-bovine serum albumin buffer (10 mM HEPES, 137.5 mM NaCl, 1.25 mM $MgCl_2$, 1.25 mM $CaCl_2$, 6 mM KCl, 10 mM glucose, 0.4 mM $NaH_2PO_4$, 0.1% bovine serum albumin (w/v), pH 7.4) (typically at $10^6$ cells/mL). Time-based recordings of the fluorescence emitted at 510 nm (excitation at 470 nm) were performed at 21° C. using a spectrofluorimeter and sampled every 0.3 s. Fluorescence binding measurements were initiated by adding at 30 s 100 nM of CXCL12-TR to the 1 mL cell suspension. For competition experiments, EGFP-CXCR4 expressing cells were preincubated for 10 min in the absence or presence of various concentrations of unlabelled drugs. Then, CXCL12-TR (100 nM) was added and fluorescence was recorded until equilibrium was reached (300 s). Data were analyzed using Kaleidagraph 3.08 software (Synergy Software, Reading, Pa., USA).

Internalization of EGFP-CXCR4 or EGFP-CXCR7.

The human CXCR7 cDNA was cloned in fusion with EGFP-cDNA into a modified pIRES Hyg 3 vector (Clonetech). HEK 293T cells stably expressing EGFP-CXCR7 was generated by the calcium phosphate-DNA co-precipitation method and were assessed for the binding of the 9C4 mAb in the absence or presence of 100 nM of CXCL12. Internalization of receptors was recorded as described in reference (Hachet-Haas et al., 2008) using cell surface labelling of EGFP with a monoclonal mouse anti-GFP (Roche Molecular Biochemicals; ¹⁄₁₀₀ dilution) as primary antibody and a R-PE-conjugated AffiniPure F(ab')₂ fragment goat antimouse IgG (Immunotech; ¹⁄₁₀₀) as secondary antibody. CXCR4 or CXCR7 staining was quantified by flow cytometric analysis (10,000 cells per sample) on a cytometer (FACScalibur, Becton-Dickinson). Mean of CXCR4 or CXCR7 fluorescence intensity was calculated using CELLQuest (Becton-Dickinson) software.

Flow Cytometry

The binding site of the peptide of SEQ ID NO 16 on CXCR4 was assessed by flow cytometry analysis (FACSCalibur; Becton Dickinson) by using the commercial anti-human CXCR4 mAb (BD Pahrmingen, clone: 12G5; or 1D9) and CCR5 mAb (BD Pahrmingen, clone: CD195). $2 \times 10^5$ Jurkat T cells were incubated with peptides at 4 C for 30 min in serum free medium. After incubation, cells were washed with FACS buffer (PBS+1% FCS) by centrifugation, then sequentially stained with either of PE labeled anti-human CXCR4 mAb or CCR5 mAb at 4 C. After being washed, the cells were fixed with 4% paraformalde-hyde in FACS buffer for 5 min at room temperature and then analyzed on a flow cytometer. Data were processed by using CELLQUEST (Becton Dickinson). To analyze receptor preference of the peptide of SEQ ID NO 16, Ghost cells (parental, X4, Hi) were harvested using Cell Dissociation Solution (Non-enzymatic 1×; Sigma: C5914) and prepared for FACS analysis as described above.

[³⁵S]GTP[S] Binding Assay

Production of recombinant baculoviruses: The production of baculoviruses encoding human CXCR4, rat G protein $α_{12}$ subunit, and both human G protein $β_1$ subunit and bovine G protein $γ_3$ subunit is described (Moepps et al., 1997). [³⁵S] GTP[S] was obtained from Perkin-Elmer (Waltham, USA). CXCL12 was obtained from PeproTech (Rocky Hill, USA).

Insect cell culture and membrane preparation: Sf9 cells were grown at 27° C. in 59 $cm^2$ cell-culture dishes in TNM-FH medium (Sigma, T 1032) supplemented with 10% fetal calf serum and 0.5 mg/ml gentamicin. For production of recombinant receptors and heterotrimeric $G_{i2}$, cells were grown to a density of approximately 60%, incubated for 1 h at 27° C. in 2 ml per dish of medium containing the recombinant baculovirus(es). The cells were then supplemented with 9 ml per dish of fresh medium and maintained in this medium for 48 h at 27° C. For preparation of a crude membrane fraction cells were pelleted by centrifugation, and resuspended in 600 µl per dish of ice-cold lysis buffer containing 20 mM Tris-HCl, pH 7.5, 1 mM EDTA, 3 µM GDP, 2 µg/ml soybean trypsin inhibitor, 1 µM pepstatin, 1 µM leupeptin, 100 µM PMSF, and 1 µg/ml aprotinin. Cells were homogenized by forcing the suspension 6 times through a 0.5 mm×23 mm needle attached to a disposable syringe. After 30 min on ice, the lysate was centrifuged at 2,450×g for 45 s to remove unbroken cells and nuclei. A crude membrane fraction was isolated from the resulting supernatant by centrifugation at 26,000×g for 30 min at 4° C. The pellet was rinsed with 300 µl of lysis buffer, resuspended in 300 µl of fresh lysis buffer, snap-frozen in liquid nitrogen, and stored at −80° C.

Binding of [$^{35}$S]GTP[S] to membranes of baculovirus-infected insect cells was assayed as described (Moepps et al., 1997). In brief, membranes (10 of protein/sample) were incubated for 60 min at 30° C. in a mixture (100 µl) containing 50 mM triethanolamine/HCl, pH 7.4, 1.0 mM EDTA, 5.0 mM MgCl$_2$, 10 µM GDP, and 1.05 nM [$^{35}$S]GTP[S] (1250 Ci/mmol). The incubation was terminated by rapid filtration through 0.45 µm pore size nitrocellulose membranes (Advanced Microdevices, Ambala Cantonment, India). The membranes were washed, dried, and the retained radioactivity was determined by liquid-scintillation counting. Nonspecific binding was defined as the binding not competed for by 100 µM unlabeled GTP[S].

GPCR Antagonist Screen of the Peptide of SEQ ID NO 16
Effect of the Peptide of SEQ ID NO 16 and Derivatives on Cell Migration Migration of Jurkat cells (ATCC) was analyzed using 6.5 mm diameter chambers with 5 µm pore filters (Transwell, 24-well cell culture, Coster, Boston, Mass.). 2×10$^5$ Jurkat cells were suspended in 200 µl Optimizer T-Cell Expansion SFM, and the cell suspensions were added to the upper chamber. Then, 10 nM CXCL12 (R&D System) and/or various concentrations of the peptide of SEQ ID NO 16 or its derivatives in 600 µl T-Cell Expansion SFM were added to the lower chamber. The cell culture chambers were incubated for 150 min in a cell culture incubator at 37° C. After incubation, chambers were removed, 100 µl of supernatants were taken and cells that migrated into the lower compartment were either counted directly using a hemocytometer or analyzed using the CellTiter-Glo Luminescent Cell Viability Assay as described above. All values represent mean numbers of migrated cells relative to CXCL12 only treated cells from a triplicate experiment±SD.

Peripheral hematopoietic stem (PHS) cells isolated by apheresis of Granulo-cyte colony-stimulating factor (G-CSF) treated individuals were obtained from the Institute of Transfusion Medicine, University Hospital Ulm). Frozen cells were carefully thawed in ⅒ diluted 10% ACD-A buffer (provided by the Institute of Transfusion Medicine) in PBS. 1×105/200 µl PHS cells were placed into the upper chamber of transwell plates. Then, 10 nM CXCL12 and/or various concentrations of the peptide of SEQ ID NO 16 or its derivatives in 600 µl culture medium were placed to each well. After 3 h, the chemotaxis was measured using the CellTiter-Glo Luminescent Cell Viability Assay as described above. All values represent mean numbers of migrated cells relative to CXCL12 only treated cells from a triplicate experiment±SD.

Cancer Cell Invasion Assay

Cell invasion of cancer cells was assayed using a Biocoat Matrigel invasion chamber (BD BioCoat™ Matrigel™ Invasion Chamber) as recommended by the manufacturer. 5×10$^4$ DU145 cells (ATCC) were suspended in 300 µl serum-free RPMI (Gibco) containing 0.1% BSA (KPL) and then added to the upper chamber. 700 µl serum-free medium with or without 100 nM CXCL12 and various concentrations of the peptide of SEQ ID NO 16 were added to each lower chamber. The chambers were incubated for 24 h at 37° C. in a humid atmosphere of 5% CO$_2$/95% air. The non-invading cells were removed from the upper surface of the membrane by scrubbing. Invaded cells toward the bottom of membrane were quantified using the CellTiter-Glo® Luminescent Cell Viability Assay kit as described above.

Effect of CXCL12 and CXCR4 Antagonists on Actin Cytoskeleton

Jurkat cells preincubated either with medium, ALB derivatives or AMD3100 (all 545 µM) were stimulated with CXCL12 (100 µg/ml) at 37° C. for the indicated time, fixed in 5% formaldehyde (Carl Roth GmBH, Karlsruhe, Germany), and permeabilized with 0.1% saponin (Carl Roth). F-actin was stained with AlexaFluor568-conjugated phalloidin (Molecular Probes, Eugene, Oreg.) followed by flow cytometric analysis of relative staining intensity.

Progenitor Cell Mobilization in Mice

C57B1/6J mice (Janvier, Le Genest St. Isle, F R) were housed in the conventional vivarium of the Goethe-University Medical Center, Frankfurt, with food and water ad libitum. Mice received i.p. injections of 200 µL water or normal saline containing 10 mg/mL the peptide of SEQ ID NO 16. Blood was drawn at the indicated times following injection from the check pouch after careful skin disinfection. After hypotonic lysis, leukocytes were incubated in duplicate in cytokine-replete commercially available semi-solid media (3434, Stem Cell Technologies, Vancouver, B C) under standard conditions. CFU—C were scored on day 7, as described (Bönig et al., 2006). CFU—C were normalized to the blood volume incubated. All animal studies were done with permission of the local IACUC, in agreement with AAALAC guidelines.

Transplantation of Mobilized Cells

C57BL/8 animals were injected with the peptide of SEQ ID NO 16 (2 mg i.p in saline) or controls saline. Peripheral blood was individually harvested 1 hour post injection, counted, combined and competitively transplanted (660 µl blood equivalent) alongside 4×10$^5$ C57BL/6 CD45.1 BM cells into C57BL/6 Cd45.1 recipients.

Asthma Mouse Model

Mice were sensitized by intraperitoneal (i.p.) injection on days 0, 1 and 2 of 50 µg ovalbumin (OVA, Sigma-Aldrich, A5503) adsorbed on 2 mg aluminium hydroxide (Sigma-Aldrich, 23918-6) in saline. Mice were challenged by intranasal (i.n.) instillation of 10 µg OVA in 25 µl saline (12.5 µl/nostril) or saline alone for control mice on days 5, 6 and 7 under anesthesia (50 mg/kg ketamine and 3.3 mg/kg xylazine, i.p.). the peptide of SEQ ID NO 16 or ALB409-423 in saline were administered i.p. (16 µmol/kg) two hours before each OVA challenge. Bronchoalveolar lavage (BAL) and differential cell counts were performed 24 h after the last OVA challenge as previously reported in (Rebber et al., 2012).

NMR Spectroscopy

For acquisition of NMR spectra, a 1 mM solution of the peptide of SEQ ID NO 16 was prepared in 10 mM Na-phosphate in H$_2$O/D$_2$O 10:1, adjusted to a final pH of 7.0 with HCl. TOCSY and NOESY $^1$H-NMR spectra were recorded at 800 MHz, 600 MHz and 500 MHz on Bruker spectrometers. The spectra acquired in the 800 MHz equipment were used due to their better quality. Spectra were referenced to external TSP, and they were recorded using the States-TPPI method incorporating the watergate 3-9-19 pulse sequence for water suppression (Jeener et al., 1979). In general, 256 equally spaced evolution-time period t$_1$ values were acquired, averaging 16 transients of 2048 points. Time-domain data matrices were all zero-filled to 4K in both dimensions, thereby yielding a digital resolution of 3.41

Hz/pt. Prior to Fourier transformation, a Lorentz-Gauss window with different parameters was applied for to both the $t_1$ and $t_2$ dimensions for all the experiments. NOESY spectra (Griesinger et al., 1988) were obtained with mixing times (0.30 s) and TOCSY experiments (Braunschweiler et al., 1983; Rucker et al., 1989) were recorded using 0.060 s DIPSI2 mixing pulses (Bartels et al., 1995). Both NOESY and TOCSY experiments were performed at 298 K.

NOESY Cross Peak Assignment and Structure Calculation

The $^1$H chemical shift dispersion in NMR spectra allowed a straightforward non-ambiguous assignment of all the NH— and CH-alpha resonances, as well as the vast majority of side-chain protons (97.7%), using standard methodology, combining TOCSY and NOESY spectroscopy. The sequential backbone connectivities were established by following the $CH_i\text{-}NH_{i+1}$ and the $NH_i\text{-}NH_{i+1}$ NOEs.

Peak lists for the NOESY spectra recorded with a 0.30 s mixing time were generated by interactive peak picking using the XEASY software (Schafer, N. 1996). NOESY cross peak volumes were determined by the automated peak integration routine, peakint (Engh 1991) implemented in XEASY. For the structure calculation, a set of 407 NOESY cross peaks were submitted to CYANA calculations (Herrmann et al., 2002; Guntert et al., 2003; Guntert et al., 2004). Of this set of signals, 400 (98.2%) were unambiguously assigned by the CYANA program. The 20 best conformers selected showed, low CYANA target function values (with mean target function: 0.056). The three-dimensional structure of the peptide of SEQ ID NO 16 was determined using the standard protocol of combined automated NOE assignment and the structure calculation of the CYANA program (version 2.1) (Herrmann et al., 2002; Guntert et al., 2003; Guntert et al., 2004). Seven cycles of combined automated NOESY assignment and structure calculations were followed by a final structure calculation. The structure calculation commenced in each cycle from 100 randomized conformers and the standard simulated annealing schedule was used. The 20 conformers with the lowest final CYANA target function values were retained for analysis and passed to the next cycle. Constraint combination was applied in the first two cycles to all NOE distance restraints, spanning at least three residues, in order to minimize structural distortion by erroneous distance restraints. The covalent parameters of Engh and Huber were used. Restraints that involved degenerate groups of protons (e.g. methyls), accidentally degenerate to methylenes, and equivalent aromatic ring protons were expanded into ambiguous distance restraints between all the corresponding pairs of hydrogen atoms. Non-degenerate diastereotopic pairs were periodically swapped for minimal target function values during simulated annealing in cycles 1-7. Weak restraints on torsion angle pairs and on side-chain torsion angles between tetrahedral carbon atoms were temporarily applied during the high-temperature and cooling phases of the simulated annealing schedule in order to favour the permitted regions of the Ramachandran plot and staggered rotamer positions, respectively. The list of upper distance bonds for the final structural calculation is exclusively comprised of unambiguously assigned upper distance bonds and does not require the possible swapping of diastereotopic pairs.

Serum Stability of the Peptide of SEQ ID NO 16

Human serum was spiked with 1 mM of the peptide of SEQ ID NO 16 or improved derivatives and incubated at 37° C. Samples were taken every two hours and immediately stored at −20° C. To assess the antiviral activity of the incubated peptide in serum, 10 µl of the samples were added to $5 \times 10^4/100$ µl TZM-bl cells. Subsequently, the cells were infected with 90 µl HIV-1 NL4-3 resulting in 20-fold dilution of peptide and serum mixtures. Infectivity was measured at 2 days after infection using the one-step Tropix Gal-Screen Kit. To assess the effect of protease inhibitors on the peptide of SEQ ID NO 16 degradation, serum was first supplemented first a protease inhibitor cocktail (1× Complete mini (Roche) and 1 mM PMSF (Roche)) before 1 MM the peptide of SEQ ID NO 16 was added.

Indirect ELISA for the Detection and Quantification of the Peptide of SEQ ID NO 16

A polyclonal antiserum against the peptide of SEQ ID NO 16 was generated by immunization of hen with the peptide of SEQ ID NO 16 peptide (Davids Biotechnologie GmbH, Regensburg), and a monoclonal antibody was generated by immunization of mice (ViroPharmaceuticals GmbH & CoKG, Hannover) as described elsewhere (Ref). To characterize reactivity and specificity of the polyclonal and monoclonal antibodies, 100 µl of serially diluted the peptide of SEQ ID NO 16, derivatives thereof (20 µM), or HSA (Sigma) were coated on ELISA plates (Corning costar) overnight at 4° C. The next day, the plates were washed twice with 200 µl ELISA washing buffer (KPL) and treated with 150 µl of 1% bovine serum albumin (BSA) in PBS to block uncoated surfaces. After additional washing, 100 µl of serially diluted mono- or polyclonal antibodies were added and incubated for 1 h. Thereafter, plates were washed and 100 µl of horseradish peroxidase (HRP)-conjugated secondary Abs (anti-chicken or anti-mouse) were added for another 1h. Thereafter plates were washed 5 times and 100 µl of SureBlue TMB 1-Component Microwell Peroxidase Substrate (KPL) was added. Color development was stopped by adding 100 µl 1 N HCl to each well and optical densities were recorded using a microtiter plate reader (Molecular Devices; VMax Kinetic Microplate Reader) at 450 nm, with 650 nm as a reference.

REFERENCES

Alkhatib, G., Combadiere, C., Broder, C. C., Feng, Y., Kennedy, P. E., Murphy, P. M., and Berger, E. A. (1996). CC CKR5: a RANTES, MIP-1alpha, MIP-1beta receptor as a fusion cofactor for macrophage-tropic HIV-1. Science 272, 1955-1958.

Bleul, C. C., Farzan, M., Choe, H., Parolin, C., Clark-Lewis, I., Sodroski, J., and Springer, T. A. (1996). The lymphocyte chemoattractant SDF-1 is a ligand for LESTR/fusin and blocks HIV-1 entry. Nature 382, 829-833.

Brelot, A., Heveker, N., Montes, M., and Alizon, M. (2000). Identification of residues of CXCR4 critical for human immunodeficiency virus coreceptor and chemokine receptor activities. J. Biol. Chem. 275, 23736-23744.

Campbell, D. J., Kim, C. H., and Butcher, E. C. (2003). Chemokines in the systemic organization of immunity. Immunol Rev. 195, 58-71.

Deng, H., Liu, R., Ellmeier, W., Choe, S., Unutmaz, D., Burkhart, M., Di Marzio, P., Marmon, S., Sutton, R. E., Hill, C. M., et al. (1996). Identification of a major co-receptor for primary isolates of HIV-1. Nature 381, 661-666.

Dragic, T., Litwin, V., Allaway, G. P., Martin, S. R., Huang, Y., Nagashima, K. A., Cayanan, C., Maddon, P. J., Koup, R. A., Moore, J. P., et al. (1996). HIV-1 entry into CD4+ cells is mediated by the chemokine receptor CC-CKR-5. Nature 381, 667-673.

Engh, R. A. and Huber, R. (1991) Accurate Bond and Angle Parameters for X-Ray Protein-Structure Refinement. Acta Crystallogr. A 47, 392-400.

Feng, Y., Broder, C. C., Kennedy, P. E., and Berger, E. A. (1996). HIV-1 entry cofactor: functional cDNA cloning of a seven-transmembrane, G protein-coupled receptor. Science 272, 872-877.

Furze, R. C., and Rankin, S. M. (2008). Neutrophil mobilization and clearance in the bone marrow. Immunology 125, 281-288.

Guntert, P. (2003) Automated NMR protein structure calculation. Prog. Nucl. Magn. Reson. Spectrosc. 43, 105-125.

Guntert, P. (2004) Automated NMR structure calculation with CYANA. *Methods Mol Biol* 278, 353-378.

Hachet-Haas M, Balabanian K, Rohmer F, Pons F, Franchet C, Lecat S, Chow K Y, Dagher R, Gizzi P, Didier B, Lagane B, Kellenberger E, Bonnet D, Baleux F, Haiech J, Parmentier M, Frossard N, Arenzana-Seisdedos F, Hibert M, Galzi J L. Small neutralizing molecules to inhibit actions of the chemokine CXCL12. J Biol Chem. 2008 Aug. 22; 283(34): 23189-99. doi: 10.1074/jbc.M803947200. Epub 2008 June 13.

Herrmann, T., Guntert, P. and Wuthrich, K. (2002) Protein NMR structure determination with automated NOE assignment using the new software CANDID and the torsion angle dynamics algorithm DYANA. J. Mol. Biol. 319, 209-227.

Huang, X., Shen, J., Cui, M., Shen, L., Luo, X., Ling, K., Pei, G., Jiang, H., and Chen, K. (2003). Molecular dynamics simulations on SDF-1alpha: binding with CXCR4 receptor. Biophys. J. 84, 171-184.

Margolis, L., and Shattock, R. (2006). Selective transmission of CCR5-utilizing HIV-1: the 'gatekeeper' problem resolved? Nat. Rev. Microbiol. 4, 312-317.

Möhle, R., and Drost, A. C. (2012). G protein-coupled receptor crosstalk and signaling in hematopoietic stem and progenitor cells. Ann. N Y Acad. Sci. 1266, 63-67.

Moepps B, Frodl R, Rodewald H R, Baggiolini M, Gierschik P. Two murine homologues of the human chemokine receptor CXCR4 mediating stromal cell-derived factor 1alpha activation of Gi2 are differentially expressed in vivo. Eur J Immunol. 1997 August; 27(8):2102-12.

Mohty, M., and Ho, A. D. (2011). In and out of the niche: perspectives in mobilization of hematopoietic stem cells. Exp. Hematol. 39, 723-729.

Moon, K. A., Kim, S. Y., Kim, T. B., Yun, E. S., Park, C. S., Cho, Y. S., Moon, H. B., and Lee, K. Y. (2007). Allergen-induced CD11b+CD11c(int) CCR3+ macrophages in the lung promote eosinophilic airway inflammation in a mouse asthma model. Int. Immunol. 19, 1371-1381.

Nagasawa, T., Hirota, S., Tachibana, K., Takakura, N., Nishikawa, S., Kitamura, Y., Yoshida, N., Kikutani, H., and Kishimoto, T. (1996). Defects of B-cell lymphopoiesis and bone-marrow myelopoiesis in mice lacking the CXC chemokine PBSF/SDF-1. Nature 382, 635-638.

Ratajczak, M. Z., and Kim, C. (2012). The use of chemokine receptor agonists in stem cell mobilization. Expert Opin. Biol. Ther. 12, 287-297.

Schäfer, N. (1996) thesis, ETH Zürich.

Schroeder, M. A., and DiPersio, J. F. (2012). Mobilization of hematopoietic stem and leukemia cells. J. Leukoc. Biol. 91, 47-57.

Tachibana, K., Hirota, S., Iizasa, H., Yoshida, H., Kawabata, K., Kataoka, Y., Kitamura, Y., Matsushima, K., Yoshida, N., Nishikawa, S., et al. (1998). The chemokine receptor CXCR4 is essential for vascularization of the gastrointestinal tract. Nature 393, 591-594.

Valenzuela-Fernández A, Palanche T, Amara A, Magerus A, Altmeyer R, Delaunay T, Virelizier J L, Baleux F, Galzi J L, Arenzana-Seisdedos F. Optimal inhibition of X4 HIV isolates by the CXC chemokine stromal cell-derived factor 1 alpha requires interaction with cell surface heparan sulfate proteoglycans. 3 Biol Chem. 2001 Jul. 13; 276(28):26550-8. Epub 2001 May 14.

Zhou, N., Luo, Z., Luo, J., Liu, D., Hall, J. W., Pomerantz, R. J., and Huang, Z. (2001). Structural and functional characterization of human CXCR4 as a chemokine receptor and HIV-1 co-receptor by mutagenesis and molecular modeling studies. J. Biol. Chem. 276, 42826-42833.

Zou, Y. R., Kottmann, A. H., Kuroda, M., Taniuchi, I., and Littman, D. R. (1998). Function of the chemokine receptor CXCR4 in haematopoiesis and in cerebellar development. Nature 393, 595-599.

The invention claimed is:

1. A peptide having at least one of the amino acid sequences selected from the group consisting of SEQ ID NO: 13, SEQ ID NO: 15, SEQ ID NO: 5, SEQ ID NO: 2, SEQ ID NO:1, SEQ ID NO: 7, SEQ ID NO: 8, SEQ ID NO: 9, SEQ ID NO: 10, SEQ ID NO: 11, SEQ ID NO: 12, and SEQ ID NO: 6.

2. A dimeric peptide consisting of two identical monomeric peptides according to claim 1, which peptides comprise or further comprise cysteine, wherein the dimeric peptides are linked to each other via a cysteine bridge which is formed between the monomeric peptides.

3. A method of treatment of a patent comprising administering a peptide of claim 1 to a patent in need thereof for treatment of stroke, cancer, cancer showing a the CRCR receptor, cancer of the liver, pancreas cancer, prostate cancer, breast cancer, infection with HIV-1, HIV-2, infection caused by *Pseudomonas,* and infection caused by *S. aureus.*

4. A method of manufacturing comprising manufacturing the peptide of claim 1 by solid phase syntheses.

5. A method of manufacturing comprising manufacturing the dimeric peptide of claim 2 wherein monomeric peptides are provided and coupled under oxidative reaction conditions and wherein SH bonds are oxidized to yield —S—S— bonds.

6. The method of claim 3 wherein the peptide is administered for treatment of HIV-1 or HIV-2.

7. The method of claim 3 wherein the peptide is administered for treatment of an infection caused by *Psuedomonas* or *S. aureus.*

8. The method of claim 3 wherein the peptide is administered for treatment of cancer.

9. The method of claim 8 wherein the cancer is pancreatic cancer.

10. The method of claim 8 wherein the cancer is breast cancer.

11. The method of claim 3 wherein the peptide is administered for treatment of stroke.

* * * * *